United States Patent [19]

Jeon

[11] Patent Number: 5,582,766
[45] Date of Patent: Dec. 10, 1996

[54] CHOLESTERIC LIQUID CRYSTAL COMPOUND, MANUFACTURING METHOD THEREOF AND DISPLAY DEVICE EMPLOYING THE SAME

[75] Inventor: Young-jae Jeon, Seoul, Rep. of Korea

[73] Assignee: Samsung Display Devices Co., Ltd., Kyungki-do, Rep. of Korea

[21] Appl. No.: 470,136

[22] Filed: Jun. 6, 1995

[30] Foreign Application Priority Data

Jan. 27, 1995 [KR] Rep. of Korea ............ 95-1586

[51] Int. Cl.$^6$ ................................. C09K 19/32
[52] U.S. Cl. ........................................ 252/299.62
[58] Field of Search ............................ 252/299.62

[56] References Cited

U.S. PATENT DOCUMENTS 5,439,613  8/1995  Takeshita et al. ............ 252/299.63

*Primary Examiner*—Cynthia Harris-Kelly
*Attorney, Agent, or Firm*—Rothwell, Figg, Ernst & Kurz

[57] ABSTRACT

A cholesteric liquid crystal compound containing a central biphenyl ester group having a rigid central group, increased molecular stability and a wide liquid crystalline phase temperature range. Accordingly, display devices employing the cholesteric liquid crystal compound can be operated at high temperatures and has good multi-color characteristics.

7 Claims, 2 Drawing Sheets

SOLID CRYSTAL

SMETIC LIQUID CRYSTAL

NEMATIC LIQUID CRYSTAL (CHOLESTERIC LIQUID CRYSTAL IF OPTICALLY ACTIVE)

ISOTROPIC LIQUID

SMETIC MESOPHASE

NEMATIC MESOPHASE

CHOLESTERIC MESOPHASE

▢ LIQUID CRYSTAL MOLECULE     ⬅ n DIRECTOR

5,582,766

CHOLESTERIC LIQUID CRYSTAL COMPOUND, MANUFACTURING METHOD THEREOF AND DISPLAY DEVICE EMPLOYING THE SAME

FIELD OF THE INVENTION

The present invention relates to a cholesteric liquid crystal compound having a central biphenyl ester group, a manufactruing method thereof and a display device employing the same.

BACKGROUND OF THE INVENTION

Generally, liquid crystal has both the fluidity of liquid and the optical properties of crystal and so is classified as a material having intermediate properties between liquid and solid. Optical anisotropy of the liquid crystal can be changed by either an electric field or heat. Liquid crystal displays (LCDs) using these properties of liquid crystal are representative of flat panel display devices along with plasma displays and electroluminescent displays.

FIG. 1 illustrates phase transition process of the liquid crystal compound according to temperature and FIG. 2 illustrates directional propertiesof the liquid crystal molecules at each liquid crystalline phase, in detail. Liquid crystal molecules in nematic mesophase are aligned in one direction and are aligned along one dimensional molecular arrangement having no regularity in the center position of the molecule. Since intermolecular interaction between terminals of the molecules is larger than attraction between adjacent molecules, sliding is generated between neighboring molecules through shear force and each molecule is orientated along the molecular chain direction. Liquid crystal molecules in smectic mesophase are aligned in two-dimensions with each molecule aligned in one direction forming a layered structure in which the end portion of each molecule is uniformly arranged with respect to a surface, simultaneously. Accordingly, liquid crystal of smectic mesophase has a larger viscosity coefficient and lower fluidity than that of nematic mesophase. In cholesteric mesophase, the molecular arrangement in one plane has a nematic structure. However, the directional factor in each plane shows a spiral shape with respect to the vertical axis as the central axis. The pitch is changed by external force such as temperature and electric fields and the reflection state of light is also changed. Accordingly, the liquid crystal of cholesteric mesophase has the diverse color changing characteristics (multichroic characteristics) and hence receives attention from application field requiring diverse colors.

Most of the conventional cholesteric liquid crystal compounds have zero or one phenyl group in the center group as shown below and have low transition temperature and inferior stability. Therefore, the compounds are not applicable in display devices operating within wide temperature ranges and phase-changed in an undesired temperature range.

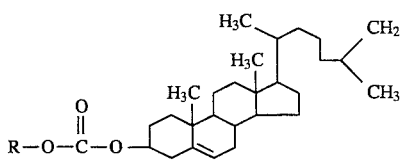

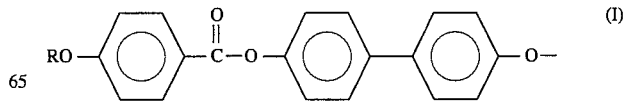

wherein, R is $C_nH_{2n+1}$ and n is an integer of 1–22.

SUMMARY OF THE INVENTION

It is an object of the present invention to provide a cholesteric liquid crystal compound having improved stability and increased transition temperature to solve the above-mentioned problem.

It is another object of the present invention to provide a method for manufacturing a cholesteric liquid crystal compound.

It is still another object of the present invention to provide a display device having a wide liquid crystalline phase temperature range which can be operated at high temperature by employing the liquid crystal compound of the present invention.

To accomplish the first object of the present invention, there is provided a cholesteric liquid crystal compound containing a central biphenyl ester group represented as formula (1) below

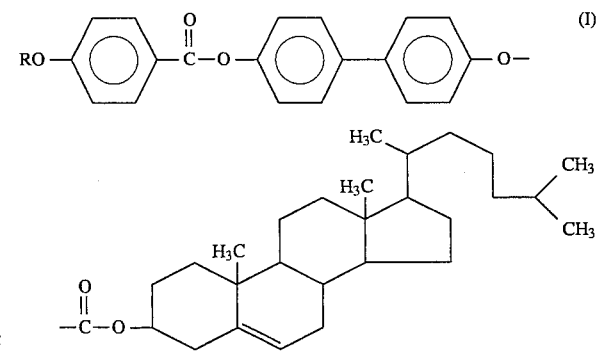

wherein, R is $C_mH_{2m+1}$ and m is an integer of 1–10.

The liquid crystalline phase temperature range of the cholesteric liquid crystal compounds of formula (I) is 75°–298° C. Smectic mesophase also can be shown.

To accomplish another object of the present invention, there is provided a method for manufacturing a cholesteric liquid crystal compound of the following formula (I) comprising the steps of; synthesizing alkoxy benzoylchloride by reacting alkoxy benzoic acid as a starting material with thionyl chloride, synthesizing intermediate material of 4-(4-alkoxybenzoyloxy)-4'-hydroxybiphenyl by reacting alkoxy benzoylchloride with 4,4'-dihydroxybiphenyl, synthesizing 4-(4-alkoxybenzoyloxy)biphenyl -4'-cholesterylcarbonate by reacting the intermediate with cholesteryl chloroformate.

-continued

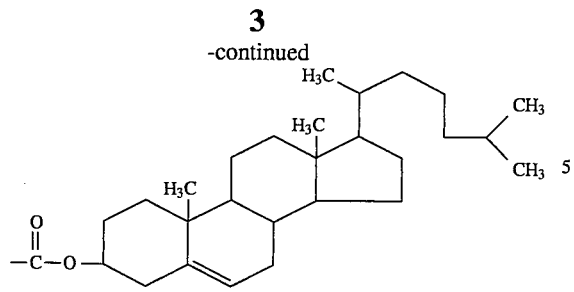

wherein, R is $C_mH_{2m+1}$ and m is an integer of 1–10.

Still another object of the present invention is accomplished by a display device having a wide range of operating temperatures by employing the cholesteric liquid crystal compound containing a central biphenyl ester group, represented as following formula (I)

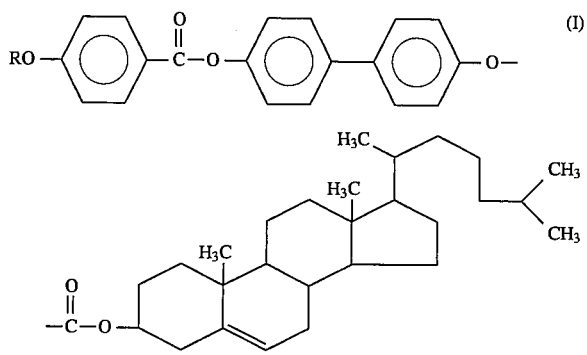

wherein, R is $C_mH_{2m+1}$ and m is an integer of 1–10.

The appropriate operating temperature range of the display device is 75°–198° C.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE INVENTION

Figure 1:
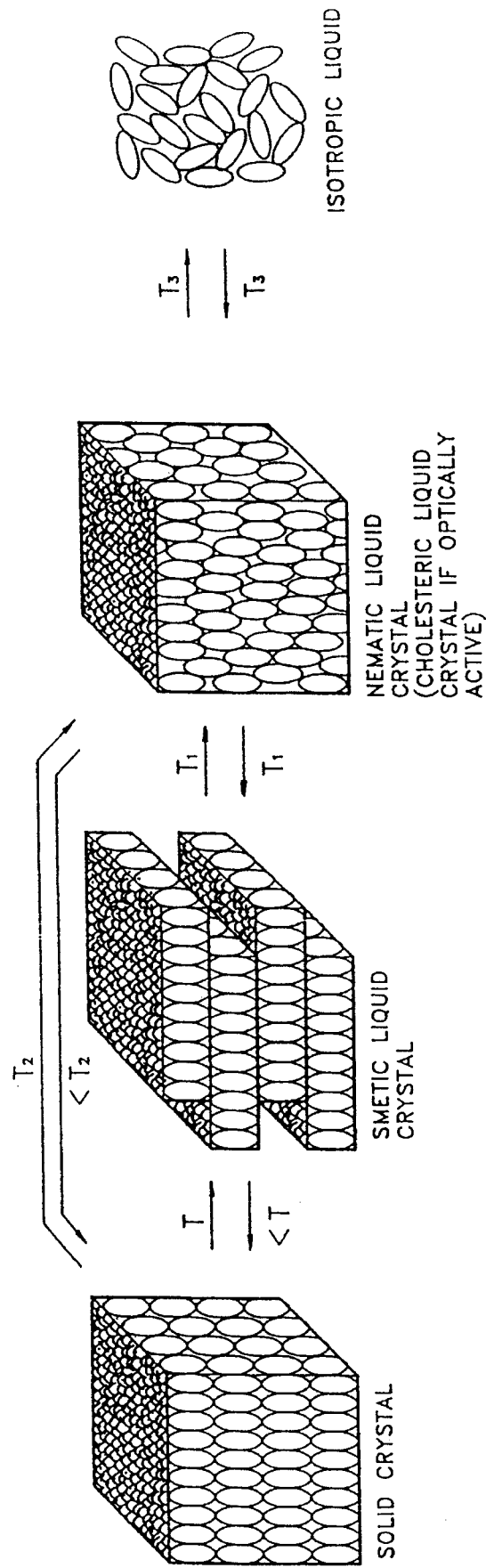
FIG. 1 illustrates the phase transition process of a liquid crystal compound according to temperature.
Figure 2:
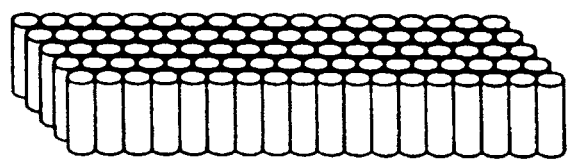
FIG. 2 illustrates the directional property of liquid crystal molecules at each liquid crystal phase in detail.
Figure 2:
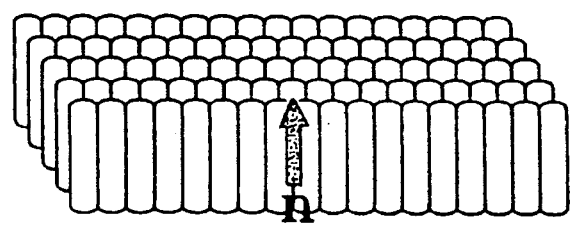
Figure 2:
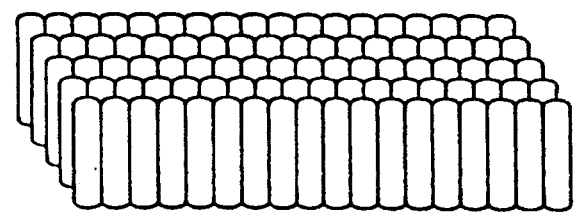
Figure 2:
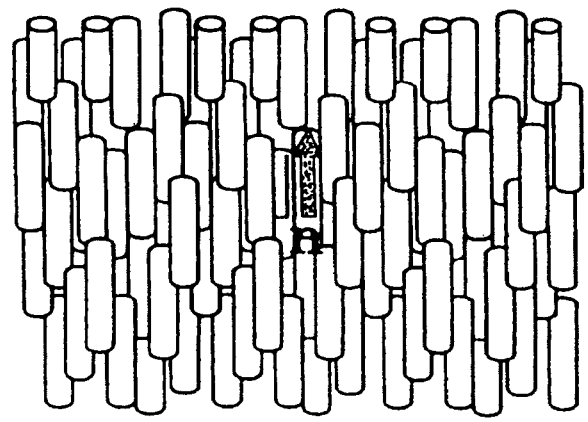
Figure 2:
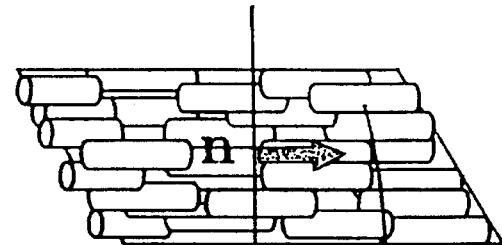
Figure 2:
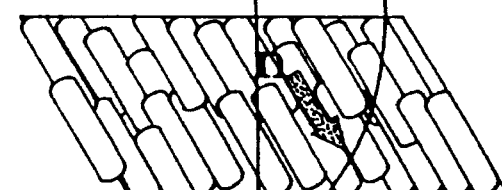
Figure 2:
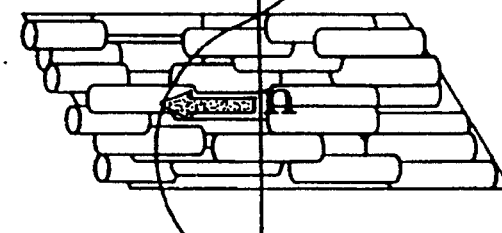
Figure 2:
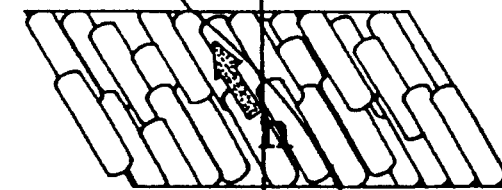
Figure 2:
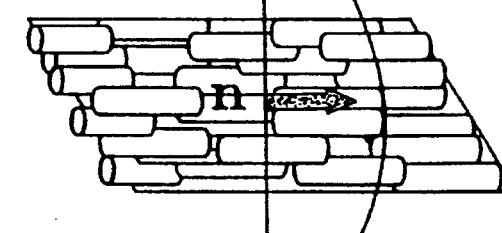

The present invention will be described in detail referring to the preferred embodiments. However, the embodiments are for explanation of the present invention and are not intended to limit the scope of the present invention thereto.

Example 1: Preparation of 4-(4-methoxybenzoyloxy)biphenyl-4'-cholesterylcarbonate (R is $CH_3$ in formula (1))

1) preparation of 4-methoxybenzoyl chloride 7.6g of 4-methoxybenzoic acid was put in a 100 ml two-necked flask and dissolved by the addition of 50 ml of thionyl chloride, the solution was then refluxed at 80° C. for 2 hours. The reaction mixture was cooled to an ambient temperature and the precipitate was filtered out. Unreacted thionyl chloride was removed and the obtained product was vacuum distilled (185° C./2 mmHg). The yield was 91% and $^1$HNMR and IR spectra of the product were as follows.

$^1$NMR ($CDCl_3$): $\delta$3.68–3.88 (2H, t), $\delta$6.68–6.80 (2H, d), $\delta$7.78–7.91 (2H, d)

IR: 1740–1755 $cm^{-1}$ (C=O, acid chloride)

B.P.: 184°–185° C.

2) preparation of 4-(4-methoxybenzoyloxy)-4'-hydroxybiphenyl 3.72 g of 4,4'-hydroxybiphenyl was put in an 100 ml two-necked flask and dissolved by the addition of 60 ml of pyridine. The flask was set up in an ice bath. 3.41 g of 4-methoxybenzoyl chloride was added over 1.5 hours while maintaining the reaction mixture at −15° C. The mixture was reacted in the ice bath for 3 hours and then at an ambient temperature for 2 hours. The reaction mixture was poured into chipped ice to obtain a white precipitate. This precipitate was filtered, dried and re-crystallized with acetone. The yield was 63% and $^1$HNMR and IR spectra of the product were as follows.

$^1$NMR ($CDCl_3$+DMSO-$d_6$): $\delta$3.85–3.97 (3H, s), $\delta$6.79–8.74 (12H, m), $\delta$9.01 (1H, s)

IR ($CCl_4$): 3470 $cm^{-1}$ (OH), 1715 (C=O)

M.P.: 184°–185° C.

3) preparation of 4-(4-methoxybenzoyloxy)biphenyl-4'-cholesterylcarbonate 1.60g of 4-(4-methoxybenzoyloxy)-4'-hydroxybiphenyl was put in an 100 ml two-necked flask and dissolved by the addition of 30 ml of pyridine. 2.25 g of cholesteryl formate was added to this solution and the mixture was refluxed for 10 hours. The reaction mixture was poured into chipped ice to obtain white precipitate. The precipitate was filtered, dried and re-crystallized with acetone three times to obtain white crystal. The yield was about 85% and $^1$HNMR analysis and elemental analysis of the product were as follows.

$^1$HNMR ($CDCl_3$+DMSO-$d_6$): $\delta$0.60–2.17 (41H, m), $\delta$2.45–2.54 (1H, s), $\delta$3.85–4.02 (3H, s), $\delta$4.50–4.62 (1H, s), $\delta$5.42–5.52 (1H, s), $\delta$6.70–8.30 (12H, m)

elemental analysis: C 78.85%, H 8.14%

Example 2–5

Compounds having ethyl, propyl, butyl and pentyl for R in formula (1) were synthesized by the same method described in example 1 except that 4-ethoxybenzoic acid, 4-propoxybenzoic acid, 4-butoxybenzoic acid and 4-pentoxybenzoic acid were used instead of 4-methoxybenzoic acid, the starting material in example 1.

Phase transition temperature of the cholesteric liquid crystal compounds prepared from examples 1–5 were measured and illustrated in Table 1.

TABLE 1

| R | | phase transition temperature (°C.) | | | | |
|---|---|---|---|---|---|---|
| $CH_3$ | K | | | 184 | CH | 298 | I |
| $C_2H_5$ | K | | | 173 | CH | 281 | I |
| $C_3H_7$ | K | 75 | S | 181 | CH | 277 | I |
| $C_4H_9$ | K | 76 | S | 175 | CH | 272 | I |
| $C_5H_{11}$ | K | 81 | S | 159 | CH | 266 | I |

K: crystalline solid, S: smectic mesophase, CH: cholesteric mesophase, I: isotropic liquid

Example 6: Manufacture of a Display Device

Transparent electrodes were coated on upper and lower substrates according to the common method for manufacturing liquid crystal device. On one substrate, sealing agent was printed for binding and sealing the upper and lower substrates, while on the other substrate, spacers were dispersed to keep a constant cell gap. The two substrates were joined together and constant force was applied while heating to cure the sealing agent and produce a void cell. Cholesteric liquid crystal compound prepared in example 3 was injected into the void cell to manufacture a display device. This display device has a very wide operating temperature range and good multichromic characteristics.

As mentioned above, cholesteric liquid crystal compound of the present invention having biphenyl and phenyl connected through an ester as the center group has a rigid center group and so has increased stability and a wide liquid crystalline phase temperature range. Accordingly, a thermometer or cholesteric display device employing the cholesteric liquid crystal compound of the present invention can be operated at high temperatures and has good multichromic characteristics.

What is claimed is:

1. A cholesteric liquid crystal compound having the formula

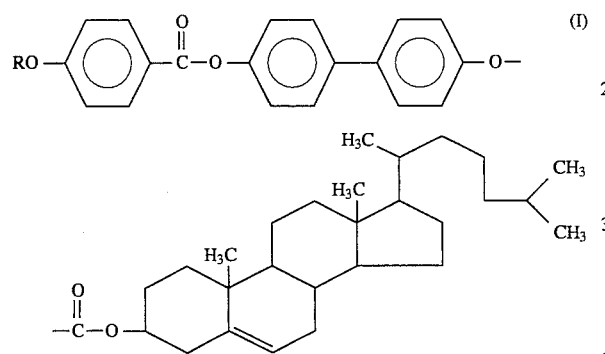

wherein, R is $C_mH_{2m+1}$ and m is an integer of 1–10.

2. A cholesteric liquid crystal compound as claimed in claim 1 having a liquid crystal phase range of 75°–298° C.

3. The cholesteric liquid crystal compound of claim 1, wherein m is an integer of 1–5.

4. A liquid crystal display device comprising a liquid crystal comprising a cholesteric liquid crystal compound having the formula (I)

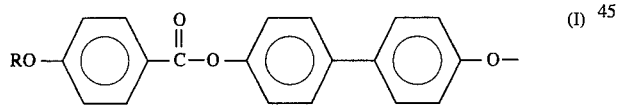

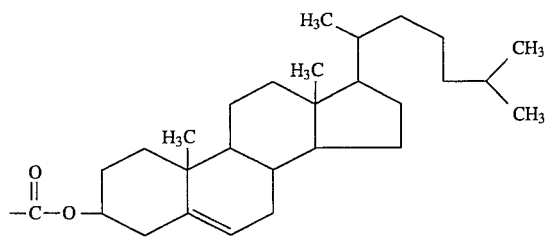

wherein R is $C_mH_{2m+1}$ and m is an integer of 1–10, and wherein the display device is operable in a temperature range of 75°–198° C.

5. The display device of claim 4, wherein m is an integer of 1–5.

6. A method for manufacturing a cholesteric liquid crystal compound of formula (I):

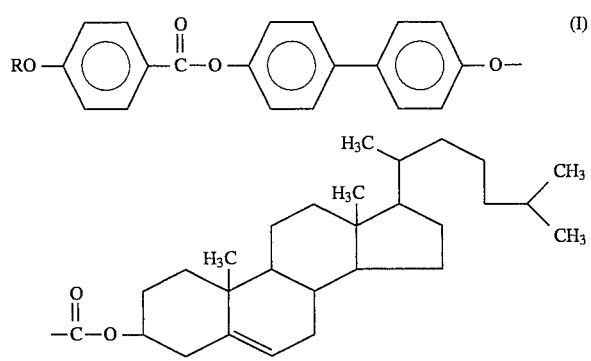

wherein R is $C_mH_{2m+1}$ and m is an integer of 1–10, comprising (a) reacting 4-(RO)benzoic acid with thionyl chloride to form 4-(RO)benzoyl chloride;

(b) reacting 4,4'-hydroxybiphenyl with the 4-(RO) benzoyl chloride from step (a) to form 4-(4-(RO) benzoyloxy) -4'-hydroxybiphenyl; and (c) reacting the 4-(4-(RO) benzoyloxy) -4'-hydroxybiphenyl from step (b) with cholesteryl chloroformate.

7. The method of claim 6, wherein m is an integer of 1–5.

* * * * *